(12) United States Patent
Beatty et al.

(10) Patent No.: US 7,930,012 B2
(45) Date of Patent: Apr. 19, 2011

(54) CHAMBER LOCATION METHOD

(75) Inventors: Graydon Ernest Beatty, St. Paul, MN (US); Jonathan Kagan, Minneapolis, MN (US); Jeffrey Robert Budd, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1966 days.

(21) Appl. No.: 10/955,894

(22) Filed: Sep. 30, 2004

(65) Prior Publication Data
US 2005/0043604 A1 Feb. 24, 2005
US 2010/0312086 A9 Dec. 9, 2010

Related U.S. Application Data

(60) Continuation of application No. 09/589,387, filed on Jun. 7, 2000, now Pat. No. 7,831,288, which is a division of application No. 08/387,832, filed as application No. PCT/US93/09015 on Sep. 23, 1993, now Pat. No. 6,240,307, which is a continuation-in-part of application No. 07/950,448, filed on Sep. 23, 1992, now Pat. No. 5,297,549, and a continuation-in-part of application No. 07/949,690, filed on Sep. 23, 1992, now Pat. No. 5,311,866, which is a continuation of application No. 10/706,484, filed on Nov. 12, 2003, now Pat. No. Re. 41,334, which is a continuation-in-part of application No. 08/376,067, filed on Jan. 20, 1995, now Pat. No. 5,553,611, which is a continuation of application No. 08/178,128, filed on Jan. 6, 1994, now abandoned.

(51) Int. Cl.
*A61B 5/042* (2006.01)

(52) U.S. Cl. .......... 600/374; 600/509; 607/122
(58) Field of Classification Search .......... 600/374, 600/372, 509; 607/115, 116, 122.123
See application file for complete search history.

(56) References Cited

U.S. PATENT DOCUMENTS

| | | | |
|---|---|---|---|
| 3,954,098 A | 5/1976 | Dick et al. | |
| 4,173,228 A | 11/1979 | Van Steenwyk et al. | |
| 4,304,239 A | 12/1981 | Perlin | |
| 4,380,237 A | 4/1983 | Newbower | |
| 4,431,005 A | 2/1984 | McCormick | |
| 4,444,195 A | 4/1984 | Gold | |
| 4,478,223 A | 10/1984 | Allor | |
| 4,522,212 A | 6/1985 | Gelinas et al. | |
| 4,559,951 A | 12/1985 | Dahl et al. | |
| 4,572,186 A | 2/1986 | Gould et al. | |
| 4,572,206 A | 2/1986 | Geddes et al. | |
| 4,573,473 A | 3/1986 | Hess | |
| 4,613,866 A | 9/1986 | Blood | |
| 4,628,937 A | 12/1986 | Hess et al. | |

(Continued)

OTHER PUBLICATIONS

"New Technique for Real-Time 3-Dimensional localization of regular intracardiac electrodes", Fred Wittkampf, et al., Circulation—Journal of the American Heart Association, Mar. 16, 2009.

(Continued)

*Primary Examiner* — Lee S Cohen
(74) *Attorney, Agent, or Firm* — Dykema Gossett PLLC

(57) ABSTRACT

A system for mapping electrical activity of a patient's heart. The system includes a set of electrodes spaced from the heart wall and a set of electrodes in contact with the heart wall. Voltage measurements from the electrodes are used to generate three-dimensional and two-dimensional maps of the electrical activity of the heart.

10 Claims, 8 Drawing Sheets

U.S. PATENT DOCUMENTS

| | | |
|---|---|---|
| 4,641,649 A | 2/1987 | Walinsky et al. |
| 4,649,924 A | 3/1987 | Taccardi |
| 4,660,571 A | 4/1987 | Hess et al. |
| 4,674,518 A | 6/1987 | Salo |
| 4,697,595 A | 10/1987 | Breyer et al. |
| 4,699,147 A | 10/1987 | Chilson et al. |
| 4,706,670 A | 11/1987 | Andersen et al. |
| 4,721,115 A | 1/1988 | Owens |
| 4,777,955 A | 10/1988 | Brayton et al. |
| 4,821,731 A | 4/1989 | Martinelli et al. |
| 4,840,182 A | 6/1989 | Carlson |
| 4,890,623 A | 1/1990 | Cook et al. |
| 4,898,176 A | 2/1990 | Petre |
| 4,898,181 A | 2/1990 | Kessler |
| 4,899,750 A | 2/1990 | Ekwall |
| 4,911,174 A | 3/1990 | Pederson et al. |
| 4,922,912 A | 5/1990 | Watanabe |
| 4,940,064 A | 7/1990 | Desai |
| 4,945,305 A | 7/1990 | Blood |
| 4,945,342 A | 7/1990 | Steinemann |
| 4,951,682 A | 8/1990 | Petre |
| 5,000,190 A | 3/1991 | Petre |
| 5,005,587 A | 4/1991 | Scott |
| 5,025,786 A | 6/1991 | Siegel |
| 5,029,588 A | 7/1991 | Yock et al. |
| 5,042,486 A | 8/1991 | Pfeiler et al. |
| 5,054,492 A | 10/1991 | Scribner et al. |
| 5,054,496 A | 10/1991 | Wen et al. |
| 5,056,517 A | 10/1991 | Fenici |
| 5,058,583 A | 10/1991 | Geddes et al. |
| 5,081,993 A | 1/1992 | Kitney et al. |
| 5,090,411 A | 2/1992 | Higuchi |
| 5,156,151 A | 10/1992 | Imran |
| 5,158,092 A | 10/1992 | Glace |
| 5,161,536 A | 11/1992 | Vilkomerson et al. |
| 5,211,165 A | 5/1993 | Dumoulin et al. |
| 5,220,924 A | 6/1993 | Frazin |
| 5,228,442 A | 7/1993 | Imran |
| 5,237,996 A | 8/1993 | Waldman et al. |
| 5,255,678 A | 10/1993 | Deslauriers et al. |
| 5,255,679 A | 10/1993 | Imran |
| 5,273,038 A | 12/1993 | Beavin |
| 5,282,471 A | 2/1994 | Sato |
| 5,295,484 A | 3/1994 | Marcus et al. |
| 5,297,549 A | 3/1994 | Beatty et al. |
| 5,305,745 A | 4/1994 | Zacouto |
| 5,311,866 A | 5/1994 | Kagan et al. |
| 5,323,781 A | 6/1994 | Ideker et al. |
| 5,324,284 A | 6/1994 | Imran |
| 5,325,860 A | 7/1994 | Seward et al. |
| 5,341,807 A | 8/1994 | Nardella |
| 5,345,936 A | 9/1994 | Pomeranz et al. |
| 5,360,006 A | 11/1994 | Geiser et al. |
| 5,372,138 A | 12/1994 | Crowley et al. |
| 5,377,678 A | 1/1995 | Dumoulin et al. |
| 5,385,146 A | 1/1995 | Goldreyer |
| 5,391,199 A | 2/1995 | Ben-Haim |
| 5,409,000 A | 4/1995 | Imran |
| 5,411,025 A | 5/1995 | Webster, Jr. |
| 5,433,198 A | 7/1995 | Desai |
| 5,433,729 A | 7/1995 | Adams et al. |
| 5,458,126 A | 10/1995 | Cline et al. |
| 5,551,426 A | 9/1996 | Hummel et al. |
| 5,553,611 A | 9/1996 | Budd et al. |
| 5,558,091 A | 9/1996 | Acker et al. |
| 5,588,432 A | 12/1996 | Crowley |
| 5,601,084 A | 2/1997 | Sheehan et al. |
| 5,622,174 A | 4/1997 | Yamazaki |
| 5,662,108 A | 9/1997 | Budd et al. |
| 5,669,382 A | 9/1997 | Curwen et al. |
| 5,687,737 A | 11/1997 | Branham et al. |
| 5,697,377 A | 12/1997 | Wittkampf |
| 5,701,897 A | 12/1997 | Sano |
| 5,713,363 A | 2/1998 | Seward et al. |
| 5,722,402 A | 3/1998 | Swanson et al. |
| 5,738,096 A | 4/1998 | Ben-Haim |
| 5,797,396 A | 8/1998 | Geiser et al. |
| 5,824,005 A | 10/1998 | Motamedi et al. |
| 5,840,031 A | 11/1998 | Crowley |
| 5,846,198 A | 12/1998 | Killmann |
| 5,848,972 A | 12/1998 | Triedman et al. |
| 5,871,019 A | 2/1999 | Belohlavek |
| 5,908,446 A | 6/1999 | Imran |
| 6,004,269 A | 12/1999 | Crowley et al. |
| 6,095,976 A | 8/2000 | Nachtomy et al. |
| 6,443,894 B1 | 9/2002 | Sumanaweera et al. |
| 6,603,996 B1 | 8/2003 | Beatty et al. |
| 6,650,927 B1 | 11/2003 | Keidar |
| 6,690,963 B2 | 2/2004 | Ben-Haim et al. |
| 6,923,768 B2 | 8/2005 | Camus et al. |
| 7,289,843 B2 | 10/2007 | Beatty et al. |
| 2002/0049375 A1 | 4/2002 | Strommer et al. |
| 2003/0093067 A1 | 5/2003 | Panescu |
| 2003/0231789 A1 | 12/2003 | Willis et al. |
| 2004/0006268 A1 | 1/2004 | Gilboa et al. |
| 2006/0058692 A1 | 3/2006 | Beatty et al. |
| 2006/0084971 A1 | 4/2006 | Beatty et al. |
| 2006/0122514 A1 | 6/2006 | Byrd et al. |

OTHER PUBLICATIONS

"New Technique for Real-Time 3-Dimensional localization of regular intracardiac electrodes", Wittkampf, Fred, et al., Circulation—Journal of the American Heart Association, Mar. 16, 1999.

Arisi, G., et al., "Localization Of Ectopic Ventricular Focuses by Means Of A Diameter Multielectrode Catheter," *Advances in Electrocardiology*, Elsevier Science Publishers B.V. (Biomedical Division), Z. Antaloczy et al., editors, pp. 67-70 (1990).

Branham B., et al., "A System for Accurate Interactive 3-D Display Of Cardiac Electrical Activity," *Computers in Cardiology*, IEEE Computer Society Press 0276-6547/92, pp. 335-338 (Oct. 11-14, 1992).

Breyer, B. and Cikes, I., "Ultrasonically Marked Catheter—A Method For Positive Echographic Catheter Position Identification," *Med. & Biol. Eng. & Comput.*, 22:268-271 (May 1984).

Buckles, D., et al., "Computer-Enhanced Mapping Of Activation Sequences In The Surgical Treatment Of Supraventricular Arrhythmias," *Pace*, vol. 13, Part I, pp. 1401-1407 (Nov. 1990).

Cikes, I., et al., "Cardiac Catheterisation Guided by Ultrasound," *Journal of the American College of Cardiology*, vol. 3, No. 2, p. 564 (Feb. 1984).

Cikes, I. and Breyer, B., "Complete Cardiac Catheterisation Guided by Ultrasound," *European Heart Journal*, vol. 4 (suppl. E), p. 21 (1983).

Cikes I., "Interventional Echocardiography," *5th Symposium on Echocardiology*, Rotterdam, Abstracts p. 38 (1983).

Cikes, I., et al., "Interventional Echocardiography," *Interventional Ultrasound*, 1st edition, chapter 25, Munksgaard, Copenhagen, pp. 160-168 (1985).

Cox, J., et al., "Surgery For Atrial Fibrillation," *Cardiac Surgery: State of the Art Reviews*, vol. 4, No. 1, pp. 207-217 (1990).

De Bakker, J., et al., "Endocardial Mapping by Simultaneous Recording Of Endocardial Electrograms During Cardiac Surgery For Ventricular Aneurysm," *Journal of American College of Cardiology*, vol. 2, No. 5, pp. 947-953 (Nov. 1983).

Derfus, D. and Pilkington, T., "Assessing The Effect Of Uncertainty In Intracavitary Electrode Position On Endocardial Potential Estimates," *IEEE Transactions on Biomedical Engineering*, vol. 39, No. 7, pp. 676-681 (Jul. 1992).

Derfus, D., et al., "Calculating Intracavitary Potentials from Measured Endocardial Potentials," *Annual International Conference of the IEEE Engineering in Medicine and Biology Society*, vol. 12, No. 2, p. 635 (1990).

Derfus, D., et al., "A Comparison of Measured and Calculated Intracavitary Potentials for Electrical Stimuli in the Exposed Dog Heart," *IEEE Transactions on Biomedical Engineering*, vol. 39, No. 11, pp. 1192-1206 (Nov. 1992).

Derfus, D. and Pilkington, T., "Effect Of Intracavitary Electrode Position On Endocardial Potential Estimates," *IEEE Engineering in Medicine & Biology Society 10th Annual International Conference*, pp. 185-186 (1988).

Desai, J., et al., "Orthogonal Electrode Catheter Array for Mapping of Endocardial Focal Site of Ventricular Activation," *Pace*, vol. 14, Part I, pp. 557-574 (Apr. 1991).

Downar, E., et al., "Endocardial Mapping of Ventricular Tachycardia in the Intact Human Ventricle: Evidence for Reentrant Mechanisms," *Journal of the American College of Cardiology*, vol. 11, No. 4, pp. 783-791 (Apr. 1988).

Durrer, D. and Van Der Tweel, L., "Spread of Activation in the Left Ventricular Wall of the Dog. II.: Activation Conditions at the Epicardial Surface," *American Heart Journal*, pp. 192-203 (Aug. 1953).

Fann, J., et al., "Endocardial Activation Mapping and Endocardial Pace-Mapping Using a Balloon Apparatus," *Am. J. Cardiol.*, vol. 55, pp. 1076-1083 (1985).

Fenici, R. and Melillo, G., "Biomagnetically Localizable Multipurpose Catheter And Method For MCG Guided Intracardiac Electrophysiology, Biopsy And Ablation Of Cardiac Arrhythmias," *International Journal of Cardiac Imaging*, vol. 7, pp. 207-215 (1991).

Fenici, R., et al., "Catheter Ablation Of Cardiac Arrhythmias: Magnetocardiographic Localization Of Electrocatheters And Arrhythmogenic Foci," *8th International Congress "The New Frontiers of Arrhythmias,"* Marilleva, Italy, pp. 723-731 (Jan. 31-Feb. 6, 1988).

Fenici, R., et al., "Clinical Magnetocardiography: 10 Years Experience At The Catholic University," *International Journal of Cardiac Imaging*, vol. 7, pp. 151-167 (1991).

Fenici, R. and Melillo, G., "Magnetocardiography: Ventricular Arrhythmias," *European Heart Journal*, vol. 14 (Suppl. E), pp. 53-60 (1993).

Harada, A., et al., "Potential Distribution Mapping: New Method For Precise Localization Of Intramural Septal Origin Of Ventricular Tachycardia," *Circulation*, vol. 78 (Suppl. III), No. 5, pp. III-137-III-147 (Nov. 1988).

Hauer, R., et al., "Endocardial Catheter Mapping: Validation Of A Cineradiographic Method for Accurate Localization Of Left Ventricular Sites," *Circulation*, vol. 74, No. 4, pp. 862-868 (Oct. 1986).

Hauer, R., et al., "Endocardial Catheter Mapping: Wire Skeleton Technique for Representation of Computed Arrhythmogenic Sites Compared With Intraoperative Mapping," *Circulation*, vol. 74, No. 6, pp. 1346-1354 (Dec. 1986).

Ideker, R., et al., "A Computerized Method For The Rapid Display Of Ventricular Activation During the Intraoperative Study Of Arrhythmias," *Circulation*, vol. 59, No. 3, pp. 449-458 (Mar. 1979).

Ideker, R., et al., "Simultaneous Multichannel Cardiac Mapping Systems," *Pace*, vol. 10, pp. 281-292 (Mar.-Apr. 1987).

Ideker, R., "A Study To Evaluate The Ability Of A Multielectrode Intracavitary Probe to Determine The Site Of Origin Of Ventricular Tachycardia," *Basic Arrhythmia Laboratory, Engineering Research Center in Emerging Cardiovascular Technologies*, Duke University, pp. 1-3.

Jackman, W., et al., "New Catheter Technique For Recording Left Free-Wall Accessory Atrioventricular Pathway Activation: Identification Of Pathway Fiber Orientation," *Circulation*, vol. 78, No. 3, pp. 598-611 (Sep. 1988).

Josephson, M., *Clinical Cardiac Electrophysiology: Techniques and Interpretations*, 2nd ed., pp. 566-580, 608-615, and 770-783 (1993).

Josephson, M., et al., "Comparison Of Endocardial Catheter Mapping With Intraoperative Mapping Of Ventricular Tachycardia," *Circulation*, vol. 61, No. 2, pp. 395-404 (Feb. 1980).

Josephson, M., et al., "Role Of Catheter Mapping In Evaluation Of Ventricular Tachycardia," *Ventricular Tachycardia—Mechanisms and Management*, pp. 309-330, Mt. Kisco, NY: Futura Publishing Co. (1982).

Josephson, M., et al., "Role Of Catheter Mapping In The Preoperative Evaluation Of Ventricular Tachycardia," *American Journal of Cardiology*, vol. 40, pp. 207-220 (Jan. 1982).

Josephson, M., et al., "Ventricular Activation During Ventricular Endocardial Pacing. II. Role Of Pace-Mapping To Localize Origin Of Ventricular Tachycardia," *The American Journal of Cardiology*, vol. 50, pp. 11-22, (Jul. 1982).

Kaltenbrunner, W., et al., "Epicardial And Endocardial Mapping Of Ventricular Tachycardia In Patients With Myocardial Infarction: Is The Origin Of The Tachycardia Always Subendocardially Localized?," *Circulation*, vol. 84, No. 3, pp. 1058-1071 (Sep. 1991).

Khoury, D. and Rudy, Y., "A Model Study Of Volume Conductor Effects On Endocardial And Intracavitary Potentials," *Circulation Research*, vol. 71, No. 3, pp. 511-525 (Sep. 1992).

Khoury, D. and Rudy, Y., "Reconstruction Of Endocardial Potentials From Intracavitary Probe Potentials: A Model Study," IEEE 0276-6547/92, pp. 9-12 (1992).

Kun, S. and Peura, R., "Conductance Volumetric Model Of An Eccentrically Positioned Catheter Within A Three-Compartment Ellipsoidal Ventricle," *IEEE Transactions on Biomedical Engineering*, vol. 40, No. 6, pp. 589-592 (Jun. 1993).

Langberg, J., et al., "The Echo-Transponder Electrode Catheter: A New Method For Mapping The Left Ventricle," *Journal of the American College of Cardiology*, vol. 12, pp. 218-223 (Jul. 1988).

Laxer, C., et al., "A Graphical Display System For Animating Mapped Cardiac Potentials," *Third Annual IEEE Symposium on Computer-Based Medical Systems*, IEEE Computer Society, pp. 197-204 (1990).

Lu, S. and Eiho, S., "Compound 3-D Visualization Of Reconstructed Coronary Arteries, Left Ventricle And Aorta From Biplane X-Ray Angiograms," *Computers in Cardiology*, IEEE Computer Society Press, 0276-6547/92, pp. 535-538 (Oct. 11-14, 1992).

Macchi, E., et al., Intracavitary Mapping: An Improved Method For Locating The Site Of Origin Of Ectopic Ventricular Beats by Means Of A Mathematical Model, *IEEE Engineering in Medicine & Biology Society 10th Annual International Conference*, pp. 0187-0188 (1988).

Macchi, E., et al., "Localization Of Ventricular Ectopic Beats From Intracavitary Potential Distributions: An Inverse Model In Terms Of Sources," *IEEE Engineering in Medicine & Biology Society 11th Annual International Conference*, pp. 0191-0192 (1989).

Masse, S., et al., "A Three-Dimensional Display For Cardiac Activation Mapping," *Pace*, vol. 14, Part I, pp. 538-545 (Apr. 1991).

Moshage, W., et al., "Biomagnetic Localization Of Ventricular Arrhythmias," *Radiology*, vol. 180, No. 3, pp. 685-692 (Sep. 1991).

Moura, L., et al., "A Microcomputer-Based Cardiac Mapping System For Recurrent Ventricular Tachycardia Surgery," *Computers in Cardiology* IEEE Computer Society Press, 0276-6547/92, pp. 431-434 (Oct. 11-14, 1992).

Pagé, P., et al., "Surgical Treatment Of Ventricular Tachycardia: Regional Cryoablation Guided by Computerized Epicardial And Endocardial Mapping," *Circulation*, vol. 80 (Suppl. I), No. 3, pp. I-124-I-134 (Sep. 1989).

Pilkington, T., et al., "Feasibility Of Estimating Endocardial Potentials From Cavity Potentials," *IEEE Ninth Annual Conference of the Engineering in Medicine and Biology Society*, IEEE, pp. 1875-1876 (1987).

Pogwizd, S. and Corr, P., "Reentrant and Nonreentrant Mechanisms Contribute To Arrhythmogenesis During Early Myocardial Ischemia: Results Using Three-Dimensional Mapping," *Circulation Research*, vol. 61, No. 3, pp. 352-371 (Sep. 1987).

Pollak, S., et al., "Intraoperative Identification Of A Radiofrequency Lesion Allowing Validation Of Catheter Mapping Of Ventricular Tachycardia With A Computerized Balloon Mapping System," *Pace*, vol. 15, pp. 854-858 (Jun. 1992).

Potratz, J., et al., "Echocardiographic Guiding Of Catheter-Electrode During Endocardial Mapping To Determine Location Of Late Fractionated Potentials In Patients With Acute Myocardial Infarction," *European Heart Journal*, vol. 12, Abstract Supplement p. 235, abstract 1242 (Aug. 1991).

Rudy, Y. and Plonsey, R., "Annotations: A Note On 'The Brody-Effect'," *J. Electrocardiology*, vol. 11, No. 1, pp. 87-90 (1978).

Rudy, Y. and Plonsey, R., "The Eccentric Spheres Model As The Basis For A Study Of The Rule Of Geometry And Inhomogeneities In Electrocardiography," *IEEE Transactions on Biomedical Engineering*, vol. BME-26, No. 7, pp. 392-399 (Jul. 1979).

Rudy, Y., et al., "The Effects Of Variations In Conductivity And Geometrical Parameters On The Electrocardiogram, Using An Eccentric Spheres Model," *Circulation Research*, vol. 44, No. 1, pp. 104-111 (Jan. 1979).

Rudy, Y. et al., "Inverse Reconstruction Of Epicardial And Endocardial Potentials: The Use Of Temporal Information," IEEE, pp. 2006-2008 (1992).

Simpson, E., et al., "Three-Dimensional Visualization Of Electrical Variables In The Ventricular Wall Of The Heart," IEEE, TH0311-1/90, pp. 190-194, (1990).

Smith, W., et al., "A Computer System for the Intraoperative Mapping of Ventricular Arrhythmias," *Computers and Biomedical Research, an International Journal*, vol. 13, No. 1, pp. 61-72 (Feb. 1980).

Smith, W. and Ideker, R., "Computer Techniques For Epicardial And Endocardial Mapping," *Progress in Cardiovascular Diseases*, vol. 26, No. 1, pp. 15-32 (Jul./Aug. 1983).

Spach, M. and Barr R., "Analysis Of Ventricular Activation And Repolarization From Intramural And Epicardial Potential Distributions For Ectopic Beats In The Intact Dog," *Circulation Research*, vol. 37, pp. 830-843 (Dec. 1975).

Stellbrink, C., et al., "Potential Of Intracardiac Ultrasonography As An Adjunct For Mapping And Ablation," *American Heart Journal*, vol. 127, No. 4, Part 2, pp. 1095-1101 (Apr. 1994).

Taccardi, B., et al., "A New Intracavitary Probe For Detecting The Site Of Origin Of Ectopic Ventricular Beats During One Cardiac Cycle," *Circulation*, vol. 75, No. 1, pp. 272-281 (Jan. 1987).

Taccardi, B., et al., "Potential Distributions And Excitation Time Maps Recorded With High Spatial Resolution From The Entire Ventricular Surface Of Exposed Dog Hearts," *Computers in Cardiology*, IEEE Computer Society Press, 0276-6547/92, pp. 1-4 (Oct. 11-14, 1992).

Tanigawa, M., et al., "Prolonged And Fractionated Right Atrial Electrograms During Sinus Rhythm In Patients With Paroxysmal Atrial Fibrillation And Sick Sinus Node Syndrome," *Journal of the American College of Cardiology*, vol. 17, No. 2, pp. 403-408 (Feb. 1991).

Tweddell, J., et al., "Potential Mapping In Septal Tachycardia: Evaluation Of A New Intraoperative Mapping Technique," *Circulation*, vol. 80 (Suppl. I), No. 3, pp. I-97- I-108 (Sep. 1989).

Witkowski, F. and Corr P., "An Automated Simultaneous Transmural Cardiac Mapping System," *American Journal of Physiology*, vol. 247, pp. H661-H668 (1984).

Young, M., et al., "A Real-Time Data Acquisition System For The Display Of Three Dimensional Cardiac Activation Maps," *Computers in Cardiology*, IEEE Computer Society Press, 0276-6547/92, pp. 331-334 (Oct. 11-14, 1992).

Yuan, S., et al., "Localization Of Cardiac Arrhythmias: Conventional Noninvasive Methods," *International Journal of Cardiac Imaging*, vol. 7, pp. 193-205 (1991).

Kristin Clingman Spencer, "*A Feasibility Study of Determining the Position of an intracavitary Multielectrode Probe Via Impedance Measurements*," Department of Electrical Engineering in the Graduate School of Duke University, 1991, pp. i-vii and 1-49.

Patrick Donahoe Wolf, "*Development and Evaluation of an Algorithm to Determine Boundary Geometry and Electrode Location from Impedance Measurements*," Department of Biomedical Engineering in the Graduate School of Duke University, 1992, pp. i-viii and 1-86.

"*New Catheter Will Find And Treat Cardiac Arrhythmias*," WPI Journal, Summer 1993, 2 pages.

"*Quickhull Algorithm For Convex Hulls*," ACM Transactions on Mathematical Software, vol. 22, No. 4, Dec. 1996, 1 page.

P. Mendler et al., "*Multichannel Recording Of Cardiac Potentials*," Medical and Biological Engineering And Computing, vol. 18, No. 5, Sep. 1980, pp. 617-624.

CHAMBER LOCATION METHOD

CROSS REFERENCE

This application is a continuation of U.S. application Ser. No. 09/589,387, filed Jun. 7, 2000, now U.S. Pat. No. 7,831,288, which in turn is a divisional of U.S. application Ser. No. 08/387,832, filed May 26, 1995, now U.S. Pat. No. 6,240,307, which in turn is a 371 of PCT/US93/09015, filed Sep. 23, 1993, which in turn is a continuation-in-part (CIP) of U.S. application Ser. No. 07/950,448, filed Sep. 23, 1992, now U.S. Pat. No. 5,297,549 and U.S. application Ser. No. 07/949,690, filed Sep. 23, 1992, now U.S. Pat. No. 5,311,866.

This application is a continuation of U.S. application Ser. No. 10/706,484, filed Nov. 12, 2003, now U.S. Pat. No. RE41,334, which is a continuation in part (CIP) of U.S. application Ser. No. 08/376,067 filed Jan. 20, 1995, now U.S. Pat. No. 5,553,611, which in turn is a continuation of U.S. application Ser. No. 08/178,128, filed Jan. 6, 1994, now abandoned. U.S. application Ser. No. 10/706,484 is a reissue application of U.S. application Ser. No. 08/387,832, filed May 26, 1995, now U.S. Pat. No. 6,240,307, which in turn is a 371 of PCT/US93/09015, filed Sep. 23, 1993, which in turn is a continuation-in-part (CIP) of U.S. application Ser. No. 07/950,448, filed Sep. 23, 1992, now U.S. Pat. No. 5,297,549 and application Ser. No. 07/949,690, filed Sep. 23, 1992, now U.S. Pat. No. 5,311,866.

TECHNICAL FIELD

The invention discloses the apparatus and technique for forming a three-dimensional electrical map of the interior of a heart chamber, and a related technique for forming a two-dimensional subsurface map at a particular location in the endocardial wall.

BACKGROUND ART

It is common to measure the electrical potentials present on the interior surface of the heart as a part of an electrophysiologic study of a patient's heart. Typically such measurements are used to form a two-dimensional map of the electrical activity of the heart muscle. An electrophysiologist will use the map to locate centers of ectopic electrical activity occurring within the cardiac tissues. One traditional mapping technique involves a sequence of electrical measurements taken from mobile electrodes inserted into the heart chamber and placed in contact with the surface of the heart. An alternative mapping technique takes essentially simultaneous measurements from a floating electrode array to generate a two-dimensional map of electrical potentials.

The two-dimensional maps of the electrical potentials at the endocardial surface generated by these traditional processes suffer many defects. Traditional systems have been limited in resolution by the number of electrodes used. The number of electrodes dictated the number of points for which the electrical activity of the endocardial surface could be mapped. Therefore, progress in endocardial mapping has involved either the introduction of progressively more electrodes on the mapping catheter or improved flexibility for moving a small mapping probe with electrodes from place to place on the endocardial surface. Direct contact with electrically active tissue is required by most systems in the prior art in order to obtain well conditioned electrical signals. An exception is a non-contact approach with spot electrodes. These spot electrodes spatially average the electrical signal through their conical view of the blood media. This approach therefore also produces one signal for each electrode. The small number of signals from the endocardial wall will result in the inability to accurately resolve the location of ectopic tissue masses. In the prior art, iso-potentials are interpolated and plotted on a rectilinear map which can only crudely represent the unfolded interior surface of the heart. Such two-dimensional maps are generated by interpolation processes which "fill in" contours based upon a limited set of measurements. Such interpolated two-dimensional maps have significant deficiencies. First, if a localized ectopic focus is between two electrode views such a map will at best show the ectopic focus overlaying both electrodes and all points in between and at worst will not see it at all. Second, the two dimensional map, since it contains no chamber geometry information, cannot indicate precisely where in the three dimensional volume of the heat chamber an electrical signal is located. The inability to accurately characterize the size and location of ectopic tissue frustrates the delivery of certain therapies such as "ablation".

SUMMARY DISCLOSURE

In general the present invention provides a method for producing a high-resolution, three-dimensional map of electrical activity of the inside surface of a heart chamber.

The invention uses a specialized catheter system to obtain the information necessary to generate such a map.

In general the invention provides a system and method which permits the location of catheter electrodes to be visualized in the three-dimensional map.

The invention may also be used to provide a two-dimensional map of electrical potential at or below the myocardial tissue surface.

Additional features of the invention will appear from the following description in which the illustrative embodiment is set forth in detail in conjunction with the accompanying drawings. It should be understood that many modifications to the invention, and in particular to the preferred embodiment illustrated in these drawings, may be made without departing from the scope of the invention.

DETAILED DISCLOSURE

Figure 1:
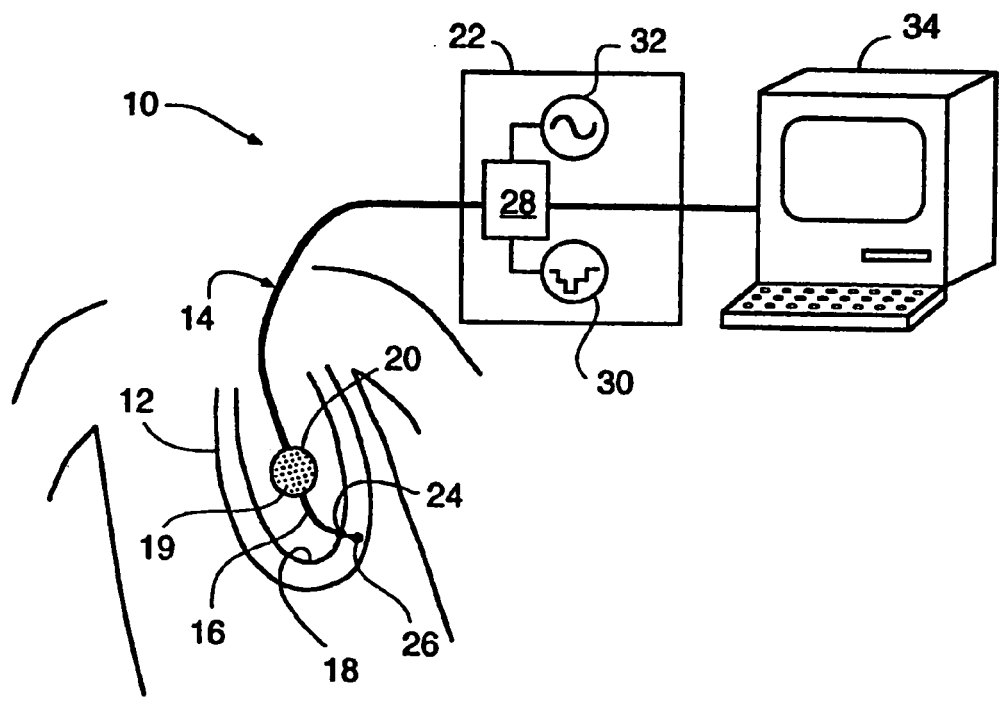
FIG. 1 is a schematic view of the system.

In general, the system of the present invention is used for mapping the electrical activity of the interior surface of a heart chamber 80. The mapping catheter assembly 14 includes a flexible lead body 72 connected to a deformable distal lead body 74. The deformable distal lead body 74 can be formed into a stable space filling geometric shape after introduction into the heart cavity 80. This deformable distal lead body 74 includes an electrode array 19 defining a number of electrode sites. The mapping catheter assembly 14 also includes a reference electrode preferably placed on a reference catheter 16 which passes through a central lumen 82 formed in the flexible lead body 72 and the distal lead body 74. The reference catheter assembly 16 has a distal tip electrode assembly 24 which may be used to probe the heart wall. This distal contact electrode assembly 24 provides a surface electrical reference for calibration. The physical length of the reference catheter 16 taken with the position of the electrode array 19 together provide a reference which may be used to calibrate the electrode array 19. The reference catheter 16 also stabilizes the position of the electrode array 19 which is desirable.

These structural elements provide a mapping catheter assembly which can be readily positioned within the heart and used to acquire highly accurate information concerning the electrical activity of the heart from a first set of preferably non-contact electrode sites and a second set of in-contact electrode sites.

The mapping catheter assembly 14 is coupled to interface apparatus 22 which contains a signal generator 32, and voltage acquisition apparatus 30. Preferably, in use, the signal generator 32 is used to measure the volumetric shape of the heart chamber through impedance plethysmography. This signal generator is also used to determine the position of the reference electrode within the heart chamber. Other techniques for characterizing the shape of the heart chamber may be substituted. Next, the signals from all the electrode sites on the electrode array 19 are presented to the voltage acquisition apparatus 30 to derive a three-dimensional, instantaneous high resolution map of the electrical activity of the entire heart chamber volume. This map is calibrated by the use of a surface electrode 24. The calibration is both electrical and dimensional. Lastly this three-dimensional map, along with the signal from an intramural electrode 26 preferably at the tip of the reference catheter 16, is used to compute a two-dimensional map of the intramural electrical activity within the heart wall. The two-dimensional map is a slice of the heart wall and represents the subsurface electrical activity in the heart wall itself.

Both of these "maps" can be followed over time which is desirable. The true three-dimensional map also avoids the problem of spatial averaging and generates an instantaneous, high resolution map of the electrical activity of the entire volume of the heart chamber and the endocardial surface. This three-dimensional map is an order of magnitude more accurate and precise than previously obtained interpolation maps. The two-dimensional map of the intramural slice is unavailable using prior techniques.

Hardware Description

FIG. 1 shows the mapping system 10 coupled to a patient's heart 12. The mapping catheter assembly 14 is inserted into a heart chamber and the reference electrode 24 touches the endocardial surface 18.

The preferred array catheter 20 carries at least twenty-four individual electrode sites which are coupled to the interface apparatus 22. The preferred reference catheter 16 is a coaxial extension of the array catheter 20. This reference catheter 16 includes a surface electrode site 24 and a subsurface electrode site 26 both of which are coupled to the interface apparatus 22. It should be understood that the electrode site 24 can be located directly on the array catheter. The array catheter 20 may be expanded into a known geometric shape, preferably spherical. Resolution is enhanced by the use of larger sized spherical shapes. A balloon 77 or the like should be incorporated under the electrode array 19 to exclude blood from the interior of the electrode array 19. The spherical shape and exclusion of blood are not required for operability but they materially reduce the complexity of the calculations required to generate the map displays.

The reference electrode 24 and/or the reference catheter 16 serves several purposes. First they stabilize and maintain the array 19 at a known distance from a reference point on the endocardial surface 18 for calibration of the shape and volume calculations. Secondly, the surface electrode 24 is used to calibrate the electrical activity measurements of the endocardial surface 18 provided by the electrode array 19.

The interface apparatus 22 includes a switching assembly 28 which is a multiplexor to sequentially couple the various electrode sites to the voltage acquisition apparatus 30, and the signal generator apparatus 32. These devices are under the control of a computer 34. The voltage acquisition apparatus 30 is preferably a 12 bit A to D convertor. A signal generator 32 is also supplied to generate low current pulses for determining the volume and shape of the endocardial chamber using impedance plethysmography, and for determining the location of the reference catheter.

The computer 34 is preferably of the "workstation" class to provide sufficient processing power to operate in essentially real time. This computer operates under the control of software set forth in the flow charts of FIGS. 12A and 12B.

Catheter Description

Figure 2:
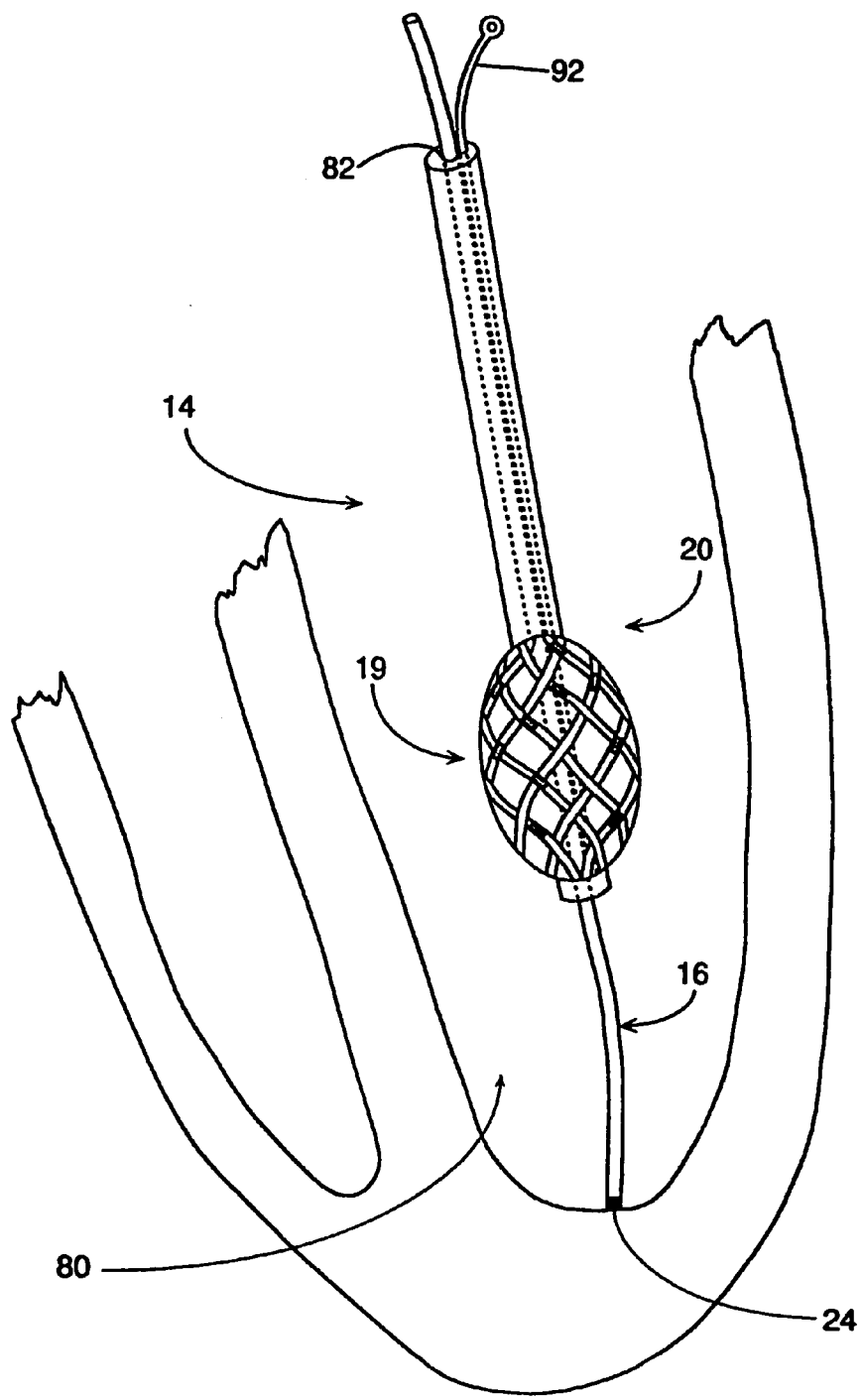
FIG. 2 is a view of the catheter assembly placed in an endocardial cavity.

FIG. 2 shows a portion of the mapping catheter assembly 14 placed into a heart chamber 80. The mapping catheter assembly 14 includes a reference catheter 16 and an array catheter 20. In FIG. 2 the array catheter 20 has been expanded through the use of a stylet 92 to place the electrode array 19 into a stable and reproducible geometric shape. The reference catheter 16 has been passed through the lumen 82 of the array catheter 20 to place a distal tip electrode assembly 24 into position against an endocardial surface. In use, the reference catheter 16 provides a mechanical location reference for the position of the electrode array 19, and the tip electrode assembly 24 provides an electrical potential reference at or in the heart wall for the mapping process.

Although the structures of FIG. 1 are preferred there are several alternatives within the scope of the invention. The principle objective of the preferred form of the catheter system is to reliably place a known collection of electrode sites away from the endocardial surface, and one or more electrode sites into contact with the endocardium. The array catheter is an illustrative structure for placing at least some of the electrode sites away from the endocardial surface. The array catheter itself can be designed to mechanically position one or more electrode sites on the endocardial surface. The reference catheter is a preferred structure for carrying one or more electrode sites and may be used to place these electrode sites into direct contact with the endocardial surface.

It should be understood that the reference catheter could be replaced with a fixed extension of the array catheter and used to push a segment of the array onto the endocardial surface. In this alternate embodiment the geometric shape of the spherical array maintains the other electrodes out of contact with the endocardial surface.

Figure 3:
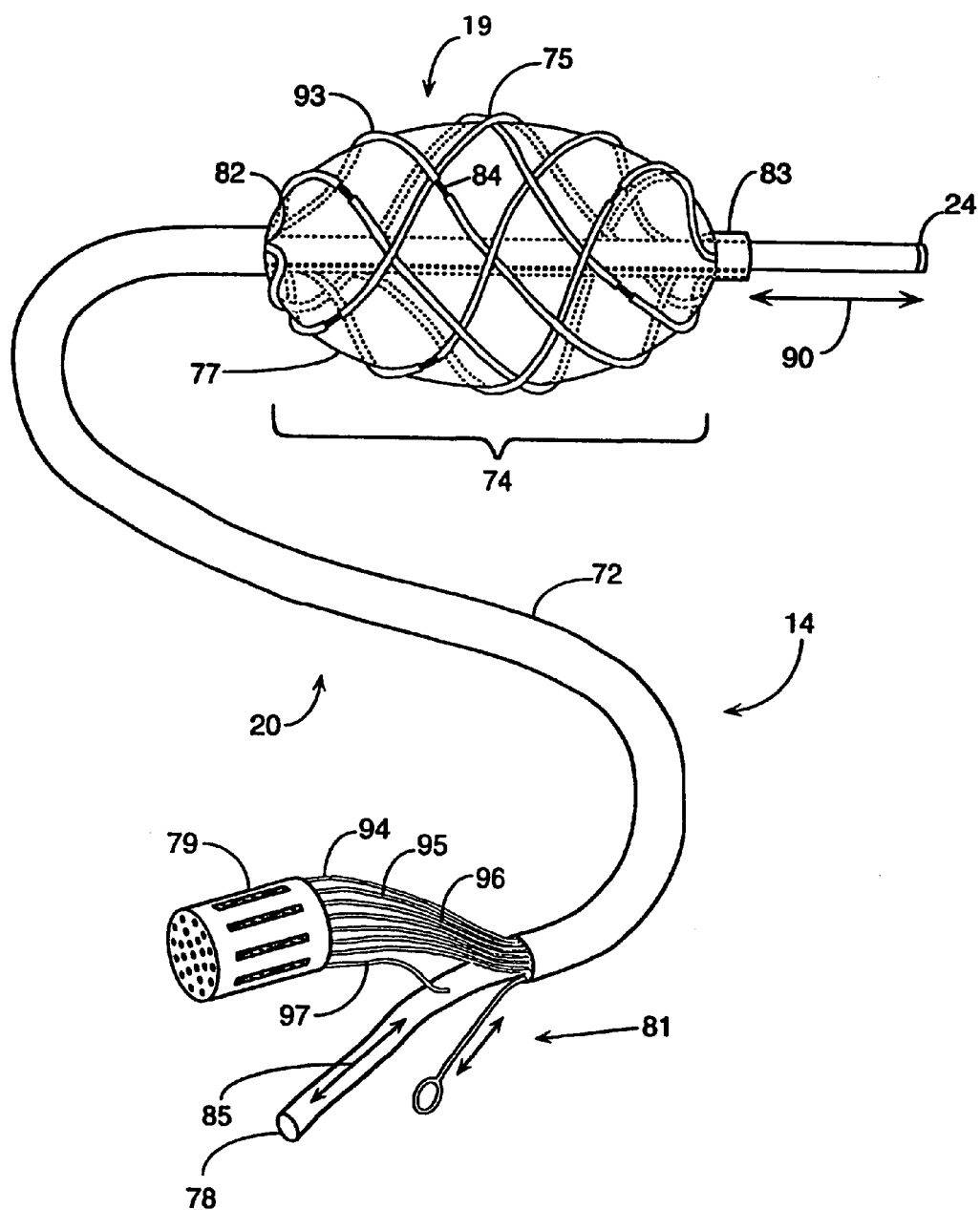
FIG. 3 is a schematic view of the catheter assembly.

FIG. 3 shows the preferred construction of the mapping catheter assembly 14 in exaggerated scale to clarify details of construction. In general, the array catheter 20 includes a flexible lead body 72 coupled to a deformable lead body 74. The deformable lead body 74 is preferably a braid 75 of insulated wires, several of which are shown as wire 93, wire 94, wire 95 and wire 96. An individual wire such as wire 93 may be traced in the figure from the electrical connection 79 at the proximal end 81 of the flexible lead body 72 through the flexible lead body 72 to the distal braid ring 83 located on the deformable lead body 74. At a predetermined location in the deformable lead body 74 the insulation has been selectively removed from this wire 93 to form a representative electrode site 84. Each of the several wires in the braid 75 may potentially be used to form an electrode site. Preferably all of the typically twenty-four to one-hundred-twenty-eight wires in the braid 75 are used to form electrode sites. Wires not used as electrode sites provide mechanical support for the electrode array 19. In general, the electrode sites will be located equidistant from a center defined at the center of the spherical array. Other geometrical shapes are usable including ellipsoidal and the like.

The proximal end 81 of the mapping catheter assembly 14 has suitable electrical connection 79 for the individual wires connected to the various electrode sites. Similarly the proximal connector 79 can have a suitable electrical connection for the distal tip electrode assembly 24 of the reference catheter 16 or the reference catheter 16 can use a separate connector. The distance 90 between the electrode array 19 and the distal tip assembly 24 electrode can preferentially be varied by sliding the reference catheter through the lumen 82, as shown by motion arrow 85. This distance 90 may be "read" at the proximal end 81 by noting the relative position of the end of the lead body 72 and the proximal end of the reference catheter 16.

Figure 4:
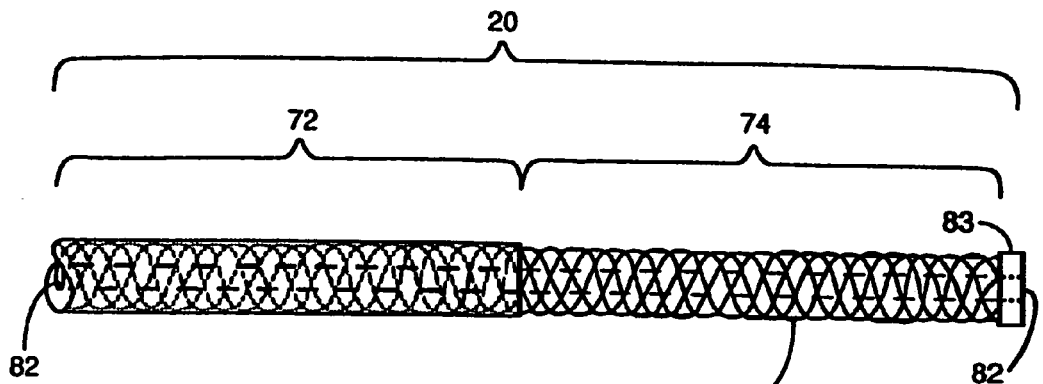
FIG. 4 is a view of the mapping catheter with the deformable lead body in the collapsed position.

FIG. 4 is a view of the mapping catheter with the deformable lead body 74 in the collapsed position.

Figure 5:
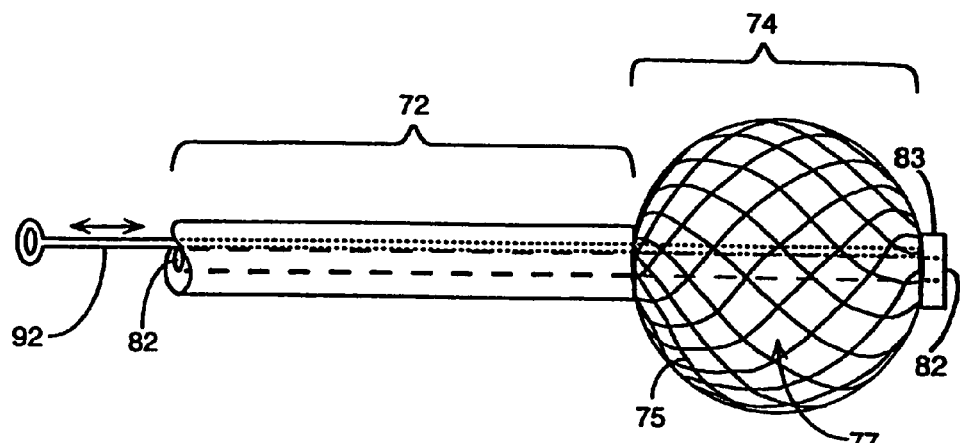
FIG. 5 is a view of the mapping catheter with the deformable lead body in the expanded position.

FIG. 5 shows that the wire stylet 92 is attached to the distal braid ring 83 and positioned in the lumen 82. Traction applied to the distal braid ring 83 by relative motion of the stylet 92 with respect to the lead body 72 causes the braid 75 to change shape. In general, traction causes the braid 75 to move from a generally cylindrical form seen in FIG. 4 to a generally spherical form seen best in FIG. 2 and FIG. 5.

The preferred technique is to provide a stylet 92 which can be used to pull the braid 75 which will deploy the electrode array 19. However, other techniques may be used as well including an optional balloon 77 shown as in FIG. 3, which could be inflated under the electrode array 19 thereby causing the spherical deployment of the array 19. Modification of the braid 75 can be used to control the final shape of the array 19. For example an asymmetrical braid pattern using differing diameter wires within the braid can preferentially alter the shape of the array. The most important property of the geometric shape is that it spaces the electrode sites relatively far apart and that the shape be predictable with a high degree of accuracy.

Figure 6:
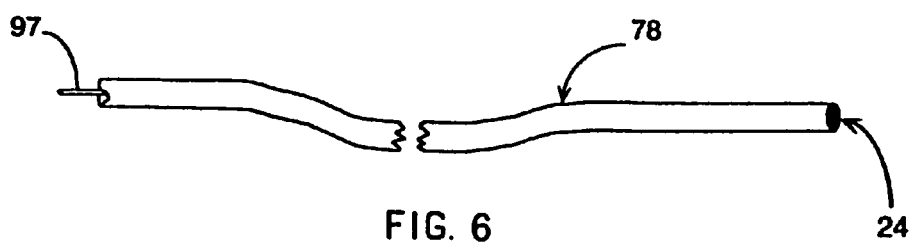
FIG. 6 is a view of the reference catheter.

FIG. 6 shows a first embodiment of the reference catheter 16 where the distal electrode assembly 24 is blunt and may be used to make a surface measurement against the endocardial surface. In this version of the catheter assembly the wire 97 (FIG. 2) communicates to the distal tip electrode and this wire may be terminated in the connector 79.

Figure 8:
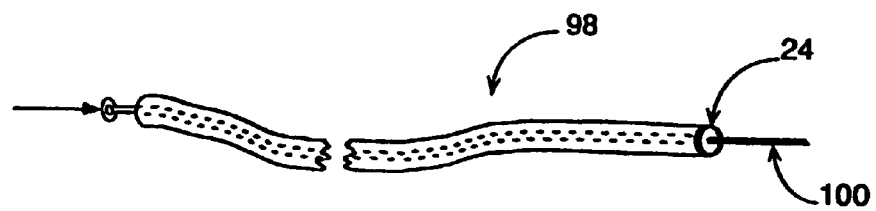
FIG. 8 is a side view of an alternate reference catheter.

FIG. 8 shows an alternate reference catheter 98 which is preferred if both surface and/or subsurface measurements of the potential proximate the endocardial surface are desired. This catheter 98 includes both a reference electrode 24 and an extendable intramural electrode body 100.

Figure 9:
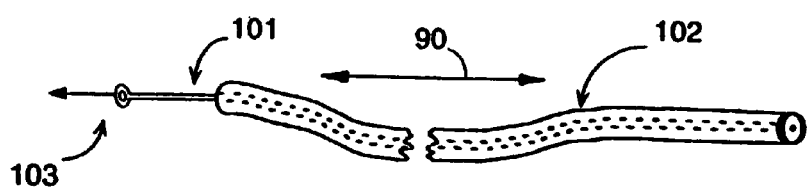
FIG. 9 is a side view of an alternate reference catheter.

FIG. 9 illustrates the preferred use of an intramural electrode stylet 101 to retract the sharp intramural electrode body 100 into the reference catheter lead body 102. Motion of the intramural electrode body 100 into the lead body 102 is shown by arrow 103.

Figure 10:
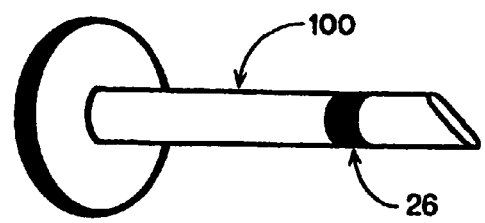
FIG. 10 is a perspective view of an alternate distal tip.

FIG. 10 shows the location of the intramural electrode site 26 on the electrode body 100. It is desirable to use a relatively small electrode site to permit localization of the intramural electrical activity.

The array catheter 20 may be made by any of a variety of techniques. In one method of manufacture, the braid 75 of insulated wires 93,94,95,96 can be encapsulated into a plastic material to form the flexible lead body 72. This plastic material can be any of various biocompatible compounds with polyurethane being preferred. The encapsulation material for the flexible lead body 72 is selected in part for its ability to be selectively removed to expose the insulated braid 75 to form the deformable lead body 74. The use of a braid 75 rather than a spiral wrap, axial wrap, or other configuration inherently strengthens and supports the electrodes due to the interlocking nature of the braid. This interlocking braid 75 also insures that, as the electrode array 19 deploys, it does so with predictable dimensional control. This braid 75 structure also supports the array catheter 20 and provides for the structural integrity of the array catheter 20 where the encapsulating material has been removed.

To form the deformable lead body 74 at the distal end of the array catheter 20, the encapsulating material can be removed by known techniques. In a preferred embodiment this removal is accomplished by mechanical removal of the encapsulating material by grinding or the like. It is also possible to remove the material with a solvent. If the encapsulating material is polyurethane, tetrahydrofuran or cyclohexanone can be used as a solvent. In some embodiments the encapsulating material is not removed from the extreme distal tip to provide enhanced mechanical integrity forming a distal braid ring 83.

With the insulated braid 75 exposed, to form the deformable lead body 74 the electrodes sites can be formed by removing the insulation over the conductor in selected areas. Known techniques would involve mechanical, thermal or chemical removal of the insulation followed by identification of the appropriate conducting wire at the proximal connector 79. This method makes it difficult to have the orientation of the proximal conductors in a predictable repeatable manner. Color coding of the insulation to enable selection of the conductor/electrode is possible but is also difficult when large numbers of electrodes are required. Therefore it is preferred to select and form the electrode array through the use of high voltage electricity. By applying high voltage electricity (typically 1-3 KV) to the proximal end of the conductor and detecting this energy through the insulation it is possible to facilitate the creation of the electrode on a known conductor at a desired location. After localization, the electrode site can be created by removing insulation using standard means or by applying a higher voltage (eg. 5 KV) to break through the insulation.

Modifications can be made to this mapping catheter assembly without departing from the teachings of the present invention. Accordingly the scope of the invention is only to be limited only by the accompanying claims.

Software Description

Figure 12:
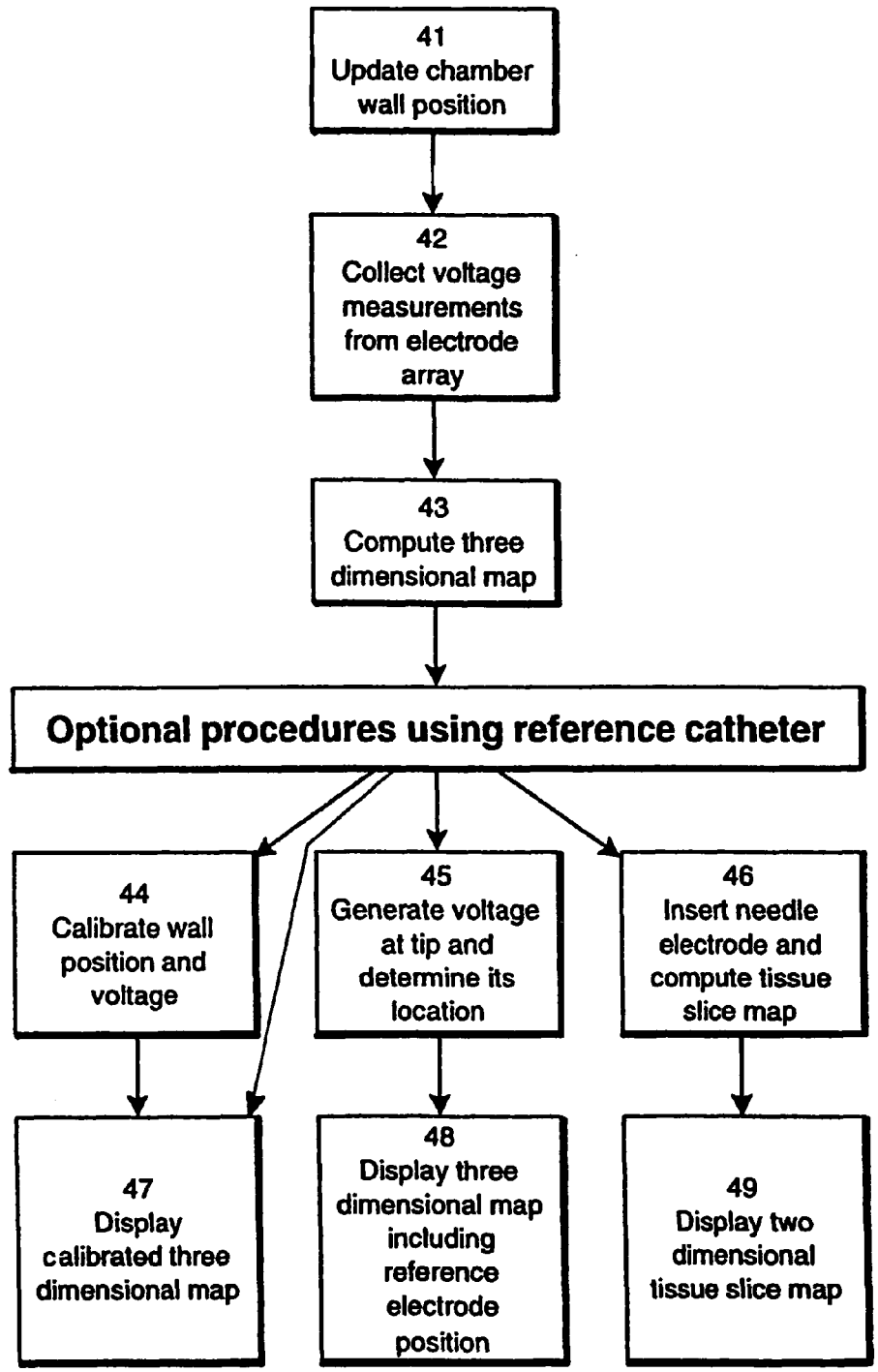
FIG. 12 is a schematic flow chart of the steps in the method.

The illustrative method may be partitioned into nine steps as shown in FIG. 12. The partitioning of the step-wise sequence is done as an aid to explaining the invention and other equivalent partitioning can be readily substituted without departing from the scope of the invention.

At step 41 the process begins. The illustrative process assumes that the electrode array assumes a known spherical shape within the heart chamber, and that there are at least twenty-four electrodes on the electrode array 19. This preferred method can be readily modified to accommodate unknown and non-reproducible, non-spherical shaped arrays. The location of each of these electrode sites on the array surface is known from the mechanical configuration of the displayed array. A method of determining the location of the electrode array 19 and the location of the heart chamber walls (cardiac geometry) must be available. This geometry measurement (options include ultrasound or impedance plethysmography) is performed in step 41. If the reference catheter 16 is extended to the chamber wall 18 then its length can be used to calibrate the geometry measurements since the calculated distance can be compared to the reference catheter length. The geometry calculations are forced to converge on the known spacing represented by the physical dimensions of the catheters. In an alternative embodiment reference electrode 24 is positioned on array catheter 20 and therefore its position would be known.

In step 42 the signals from all the electrode sites in the electrode array 19 are sampled by the A to D converter in the voltage acquisition apparatus 30. These measurements are stored in a digital file for later use in following steps. At this point (step 43) the known locations of all the electrodes on the electrode array 19 and the measured potentials at each electrode are used to create the intermediate parameters of the three-dimensional electrical activity map. This step uses field theory calculations presented in greater detail below. The components which are created in this step ($F_{lm}$) are stored in a digital file for later use in following steps.

At the next stage the question is asked whether the reference catheter 16 is in a calibrating position. In the calibrating position, the reference catheter 16 projects directly out of the array catheter 20 establishing a length from the electrode array 19 which is a known distance from the wall 18 of the heart chamber. This calibration position may be confirmed using fluoroscopy. If the catheter is not in position then the process moves to step 45, 46 or 47.

If the reference catheter 16 is in the calibrating position then in step 44 the exact position of the reference catheter 16 is determined using the distance and orientation data from step 41. The available information includes position in space of the reference catheter 16 on the chamber wall 18 and the intermediate electrical activity map parameters of the three-dimensional map. Using these two sets of information the expected electrical activity at the reference catheter surface electrode site 24 is determined. The actual potential at this site 24 is measured from the reference catheter by the A to D converter in the voltage acquisition apparatus 30. Finally, a scale factor is adjusted which modifies the map calculations to achieve calibrated results. This adjustment factor is used in all subsequent calculations of electrical activity.

At step 47 the system polls the user to display a three-dimensional map. If such a map is desired then a method of displaying the electrical activity is first determined. Second an area, or volume is defined for which the electrical activity is to be viewed. Third a level of resolution is defined for this view of the electrical activity. Finally the electrical activity at all of the points defined by the display option, volume and resolution are computed using the field theory calculations and the adjustment factor mentioned above. These calculated values are then used to display the data on computer 34.

Figure 7:
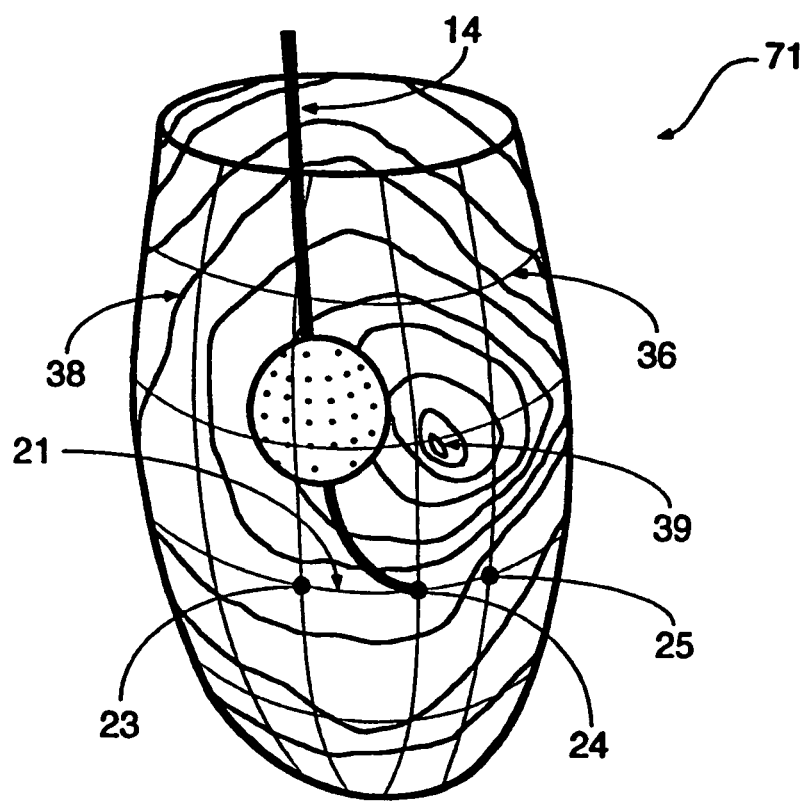
FIG. 7 is a schematic view representing the display of the three-dimensional map.

FIG. 7 is a representative display 71 of the output of process 47. In the preferred presentation the heart is displayed as a wire grid 36. The iso-potential map for example is overlaid on the wire grid 36 and several iso-potential lines such as iso-potential or isochrone line 38 are shown on the drawing. Typically the color of the wire grid 36 and the iso-potential or isochrone lines will be different to aid interpretation. The potentials may preferably be presented by a continuously filled color-scale rather than iso-potential or isochrone lines. The tightly closed iso-potential or isochrone line 39 may arise from an ectopic focus present at this location in the heart. In the representative display 71 of process 47 the mapping catheter assembly will not be shown.

In step 45 a subthreshold pulse is supplied to the surface electrode 24 of the reference catheter 16 by the signal generator 32. In step 54 the voltages are measured at all of the electrode sites on the electrode array 19 by the voltage acquisition apparatus 30. One problem in locating the position of the subthreshold pulse is that other electrical activity may render it difficult to detect. To counteract this problem step 55 starts by subtracting the electrical activity which was just measured in step 44 from the measurements in step 54. The location of the tip of the reference catheter 16 (i.e. surface electrode 24), is found by first performing the same field theory calculations of step 45 on this derived electrode data. Next, four positions in space are defined which are positioned near the heart chamber walls. The potentials at these sites are calculated using the three-dimensional electrical activity map. These potentials are then used to triangulate, and thus determine, the position of the subthreshold pulse at the surface electrode 24 of the reference catheter 16. If more accurate localization is desired then four more points which are much closer to the surface electrode 24 can be defined and the triangulation can be performed again. This procedure for locating the tip of the reference catheter 16 can be performed whether the surface electrode 24 is touching the surface or is located in the blood volume and is not in contact with the endocardial surface.

At step 48 the reference catheter's position in space can be displayed by superimposing it on the map of electrical activity created in step 47. An example of such a display 71 is presented in FIG. 7.

Figure 11:
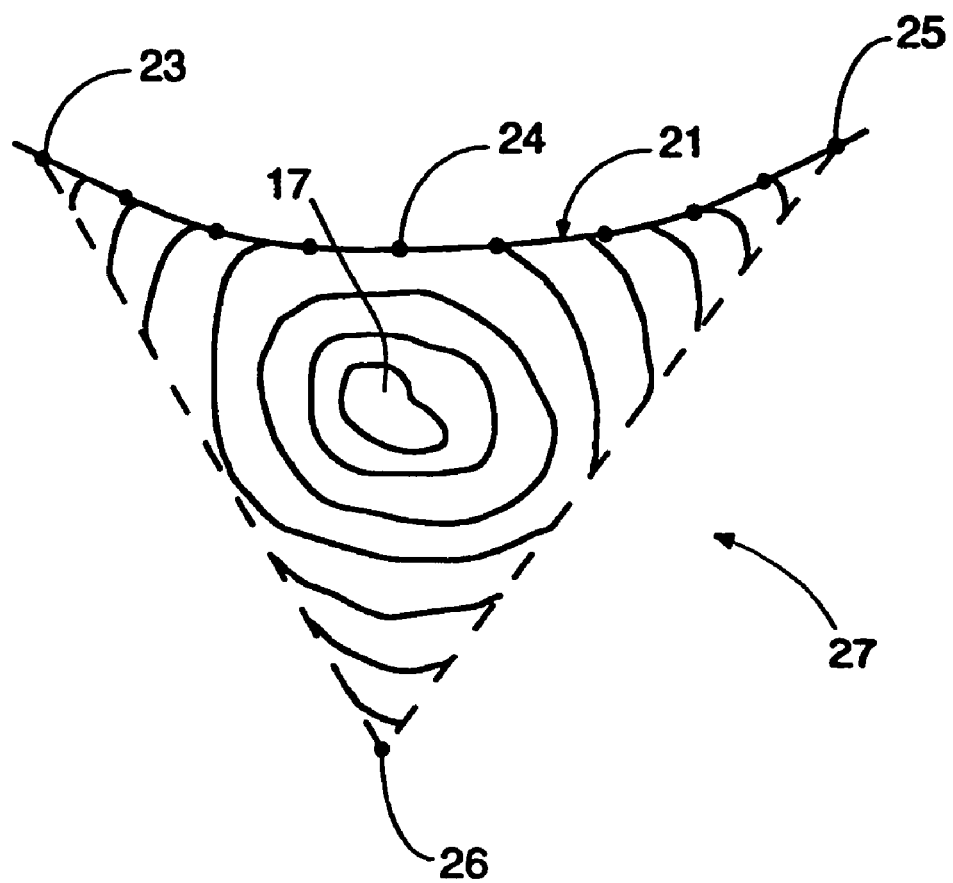
FIG. 11 is a schematic view representing the display of the subsurface two-dimensional map.

When step 46 is reached the surface electrode 24 is in a known position on the endocardial surface 18 of the heart chamber which is proper for determining the electrical activity of the tissue at that site. If the intramural or subsurface extension 100 which preferentially extends from the tip of the reference catheter 102 is not inserted into the tissue then the user of the system extends the subsurface electrode 26 into the wall 18. The potentials from the surface electrode 24 and from the intramural subsurface 26 electrode are measured by voltage acquisition apparatus 30. Next a line 21 along the heart chamber wall which has the surface electrode 24 at its center is defined by the user of the system. The three-dimensional map parameters from step 43 are then used to compute a number of points along this line including the site of the reference catheter surface electrode 24. These calculations are adjusted to conform to the measured value at the reference catheter surface electrode 24. Next a slice of tissue is defined and bounded by this line 21 (FIG. 7) and the location of the intramural subsurface electrode 26 (FIG. 11) and computed positions such as 23 and 25. Subsequently a two-dimensional map 27 of the electrical activity of this slice of tissue is computed using the center of gravity calculations detailed below in the section on algorithm descriptions. Points outside of the boundary of the slice cannot be computed accurately. In step 49 this map 27 of electrical activity within the two-dimensional slice is displayed as illustrated in FIG. 11. In this instance the iso-potential line 17 indicates the location within the wall 18 of the ectopic focus.

Description of the Preferred Computing Algorithms

Two different algorithms are suitable for implementing different stages of the present invention.

The algorithm used to derive the map of the electrical activity of the heart chamber employs electrostatic volume-conductor field theory to derive a high resolution map of the chamber volume. The second algorithm is able to estimate intramural electrical activity by interpolating between points on the endocardial surface and an intramural measurement using center of gravity calculations.

In use, the preliminary process steps identify the position of the electrode array 19 consequently the field theory algorithm can be initialized with both contact and non-contact type data. This is one difference from the traditional prior art techniques which require either contact or non-contact for accurate results, but cannot accommodate both. This also permits the system to discern the difference between small regions of electrical activity close to the electrode array 19 from large regions of electrical activity further away from the electrode array 19.

In the first algorithm, from electrostatic volume-conductor field theory it follows that all the electrodes within the solid angle view of every locus of electrical activity on the endocardial surface are integrated together to reconstruct the electrical activity at any given locus throughout the entire volume and upon the endocardium. Thus as best shown in FIG. 7 the signals from the electrode array 19 on the catheter 20 produce a continuous map of the whole endocardium. This is another difference between the present method and the traditional prior art approach which use the electrode with the lowest potential as the indicator of cardiac abnormality. By using the complete information in the algorithm, the resolution of the map shown in FIG. 7 is improved by at least a factor of ten over prior methods. Other improvements include: the ability to find the optimal global minimum instead of sub-optimal local minima; the elimination of blind spots between electrodes; the ability to detect abnormalities caused by multiple ectopic foci; the ability to distinguish between a localized focus of electrical activity at the endocardial surface and a distributed path of electrical activity in the more distant myocardium; and the ability to detect other types of electrical abnormalities including detection of ischemic or infarcted tissue.

The algorithm for creating the 3D map of the cardiac volume takes advantage of the fact that myocardial electrical activity instantaneously creates potential fields by electrotonic conduction. Since action potentials propagate several orders of magnitude slower than the speed of electrotonic conduction, the potential field is quasi-static. Since there are no significant charge sources in the blood volume, Laplace's Equation for potential completely describes the potential field in the blood volume:

$$-\nabla^2 f = 0$$

LaPlace's equation can be solved numerically or analytically. Such numerical techniques include boundary element analysis and other interative approaches comprised of estimating sums of nonlinear coefficients.

Specific analytical approaches can be developed based on the shape of the probe (i.e. spherical, prolate spherical or cylindrical). From electrostatic field theory, the general spherical harmonic series solution for potential is:

$$f(r, q, j) = \overset{l=0}{\underset{\infty}{\hat{A}}} \hat{A}_m = l?l\{A_l r^l + Bl r^{-(l-1)}\} f_{lm} y_{lm}(q, j)$$

In spherical harmonics, $Y_{lm}(q,j)$ is the spherical harmonic series made up of Legendre Polynomials. $F_{lm}$ is the $lm^{th}$ component of potential and is defined as:

$$f_{lm} = \acute{U} V(q,j) Y_{lm}(q,j) dW$$

$$dW = \sin q \, dq \, dj$$

where V(q,j) is the measured potential over the probe radius R and dW is the differential solid angle and, in spherical coordinates, is defined as:

During the first step in the algorithmic determination of the 3D map of the electrical activity each $F_{lm}$ component is determined by integrating the potential at a given point with the spherical harmonic at that point with respect to the solid angle element subtended from the origin to that point. This is an important aspect of the 3D map; its accuracy in creating the 3D map is increased with increased numbers of electrodes in the array and with increased size of the spherical array. In practice it is necessary to compute the $F_{lm}$ components with the subscript l set to 4 or greater. These $F_{lm}$ components are stored in an l by m array for later determination of potentials anywhere in the volume within the endocardial walls.

The bracketed expression of equation 1 (in terms of $A_l$, $B_l$, and r) simply contains the extrapolation coefficients that weight the measured probe components to obtain the potential components anywhere in the cavity. Once again, the weighted components are summed to obtain the actual potentials. Given that the potential is known on the probe boundary, and given that the probe boundary is non-conductive, we can determine the coefficients $A_l$ and $B_l$, yielding the following final solution for potential at any point within the boundaries of the cavity, using a spherical probe of radius R:

$$f(r, q, j) = \overset{\infty}{\underset{l=0}{\hat{A}}} \overset{l}{\underset{m=-l}{\hat{A}}} \left[ \left(\frac{l+1}{2l+1}\right) \left(\frac{r}{R}\right)^l + \left(\frac{l}{2l+1}\right) \left(\frac{r}{R}\right)^{-l-1} \right] f_{lmlm}(q, j)$$

On exemplary method for evaluating the integral for $F_{lm}$ is the technique of Filon integration with an estimating sum, discretized by p latitudinal rows and q longitudinal columns of electrodes on the spherical probe.

$$f_{lm} \geq \frac{4p}{pq} \overset{p}{\underset{i=1}{S}} \overset{q}{\underset{j=1}{S}} V(q_i, j_j) Y_{lm}(q_i, j_j)$$

Note that p times q equals the total number of electrodes on the spherical probe array. The angle q ranges from zero to p radians and j ranges from zero to 2p radians.

At this point the determination of the geometry of the endocardial walls enters into the algorithm. The potential of each point on the endocardial wall can now be computed by defining them as r, q, and j. During the activation sequence the graphical representation of the electrical activity on the endocardial surface can be slowed down by 30 to 40 times to present a picture of the ventricular cavity within a time frame useful for human viewing.

A geometric description of the heart structure is required in order for the algorithm to account for the inherent effect of spatial averaging within the medium (blood). Spatial averaging is a function of both the conductive nature of the medium as well as the physical dimensions of the medium.

Given the above computed three-dimensional endocardial potential map, the intramural activation map of FIG. 11 is estimated by interpolating between the accurately computed endocardial potentials at locations 23 and 25 (FIG. 7), and actual recorded endocardial value at the surface electrode 24 and an actual recorded intramural value at the subsurface electrode 26 site. This first-order estimation of the myocardial activation map assumes that the medium is homogenous and that the medium contains no charge sources. This myocardial activation estimation is limited by the fact that the myocardial medium is not homogeneous and that there are charge sources contained within the myocardial medium. If more than one intramural point was sampled the underlying map of intramural electrical activity could be improved by interpolating between the endocardial surface values and all the sample intramural values. The center-of-gravity calculations can be summarized by the equation:

$$V(\overline{r_x}) = \frac{\overset{n}{\underset{i=1}{S}} V_i(\Omega \overline{r_x} - \overline{r_i}\Omega^{-k})}{\overset{n}{\underset{i=1}{S}} \Omega \overline{r_x} - \overline{r_i}\Omega^{-k}}$$

where, $V_{(x)}$ represents the potential at any desired point defined by the three-dimensional vector $_x$ and, $V_i$ represents each of n known potentials at a point defined by the three-dimensional vector $_i$ and, k is an exponent that matches the physical behavior of the tissue medium.

From the foregoing description, it will be apparent that the method for determining a continuous map of the electrical activity of the endocardial surface of the present invention has a number of advantages, some of which have been described above and others of which are inherent in the invention. Also modifications can be made to the mapping probe without departing from the teachings of the present invention. Accordingly the scope of the invention is only to be limited as necessitated by the accompanying claims.

The invention claimed is:

1. A method of locating a catheter having a location electrode in an endocardial cavity, the method comprising the steps of:
 a) positioning an electrode array within the endocardial cavity;
 b) positioning the catheter within the endocardial cavity;
 c) supplying an electric pulse to the location electrode;
 d) receiving at the electrode array the voltage relating to the electric pulse; distinguishing the received voltage relating to the electric pulse from any voltage relating to other electrical activity; and
 e) performing field theory calculations upon voltage data received from said electrode array to determine the location of the location electrode within the endocardial cavity.

2. The method of claim 1, wherein the endocardial cavity is a ventricular cavity.

3. The method of claim 1, further comprising the step of f) displaying the position of the location electrode on an image representing the shape of the endocardial cavity.

4. The method of claim 2, wherein the endocardial cavity is the right ventricular cavity.

5. The method of claim 3, further comprising: the step of g) calculating and displaying a map of electrical activity in the endocardial cavity and superimposing the location of the location electrode on the map of electrical activity.

6. The method of claim 5, wherein the step of calculating and displaying a map of electrical activity in the endocardial cavity includes the substeps of:
 i) determining volume and shape of the endocardial cavity;
 ii) measuring electrical potentials on the electrode array relating to the electrical activity of the endocardial cavity;
 iii) calculating the electrical activity of the endocardial cavity based upon the measured electric potentials and the volume and shape of the endocardial cavity.

7. A method of locating a catheter having a location electrode in a body cavity, the method comprising the steps of:
 a) positioning the location electrode of the catheter within the body cavity;
 b) supplying an electric pulse to the location electrode;
 c) receiving at a plurality of mapping electrodes the voltage relating to the electric pulse; and
 d) performing calculations to determine the location of the location electrode using the received voltages.

8. The method of claim 7, wherein the body cavity is an endocardial cavity, and further comprising the steps of:
 e) positioning the location electrode proximal to a wall of the endocardial cavity; and
 f) sensing the electrical activity of the endocardial wall proximal to the location electrode.

9. The method of claim 8, further comprising the steps of:
 g) generating a geometrical map of the endocardial cavity; and
 h) indicating on the map the location of the catheter.

10. The method of claim 9, further comprising the step of:
 i) displaying on the map the electrical activity sensed in step f.

* * * * *